US006348469B1

(12) United States Patent
Seth (10) Patent No.: US 6,348,469 B1
(45) Date of Patent: *Feb. 19, 2002

(54) SOLID COMPOSITIONS CONTAINING GLIPIZIDE AND POLYETHYLENE OXIDE

(75) Inventor: Pawan Seth, Irvine, CA (US)

(73) Assignee: Pharma Pass LLC, Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/579,392

(22) Filed: May 26, 2000

Related U.S. Application Data (63) Continuation-in-part of application No. 08/943,304, filed on Oct. 14, 1997, now Pat. No. 6,117,453, which is a continuation of application No. PCT/FR96/00574, filed on Apr. 15, 1996.

(30) Foreign Application Priority Data

Apr. 14, 1995 (FR) .............................. 95 04520

(51) Int. Cl.$^7$ .............................. A61K 31/495
(52) U.S. Cl. ....................................... 514/255
(58) Field of Search ......................... 514/255

(56) References Cited

U.S. PATENT DOCUMENTS

| | | |
|---|---|---|
| 4,343,789 A | 8/1982 | Kawata et al. |
| 4,404,183 A | 9/1983 | Kawata et al. |
| 4,764,378 A | 8/1988 | Keith et al. |
| 5,037,653 A | 8/1991 | Dawson |
| 5,273,758 A | 12/1993 | Royce |
| 5,354,560 A | 10/1994 | Lovrecich |
| 5,378,474 A | 1/1995 | Morella et al. |
| 5,580,578 A | 12/1996 | Oshlack et al. |
| 5,654,005 A | 8/1997 | Chen et al. |
| 5,766,623 A | 6/1998 | Ayres et al. |
| 6,117,453 A * | 9/2000 | Seth et al. .................. 574/255 |

FOREIGN PATENT DOCUMENTS

EP      0 277 092 B1      1/1988

OTHER PUBLICATIONS

Hawley's, Condensed Chemical Dictionary, 12th Edition, 1993, p. 71.
CRC Handbook of Chemistry and Physics, 65th Edition, 1984–1985, p. F–67.
The Theory and Practice of Industrial Pharmacy, 1970, pp. 253–255.
Remington's Pharmaceutical Sciences, 14th Edition, 1970, p. 182.
General Chemistry, Chapter 8 –The Chemical Bond, 1992, pp. 314–315.
Encyclopedia of Pharmaceutical Technology, James Swarbrick and James C. Boylan, vol. 1, pp. 12–13 (1990).

* cited by examiner

Primary Examiner—Theodore J. Criares
(74) Attorney, Agent, or Firm—Harness, Dickey & Pierce, P.L.C.

(57) ABSTRACT

The invention provides a solid composition comprising glipizide which is not in an amorphous form; polyethylene oxide; the balance consisting of conventional additives; and a functional coating; exhibiting a dissolution profile such that after 4 hours, from 10 to 30% of the glipizide is released, after 8 hours, from 40 to 60% of the glipizide is released, after 12 hours, from 80 to 100% of the glipizide is released.

8 Claims, 1 Drawing Sheet

FIGURE

SOLID COMPOSITIONS CONTAINING GLIPIZIDE AND POLYETHYLENE OXIDE

This is a continuation-in-part of U.S. patent application Ser. No. 08/943,304, filed Oct. 14, 1997, now U.S. Pat. No. 6,117,453 which is a continuation of PCT/FR96/00574 filed Apr. 15, 1996.

The present invention relates to novel solid compositions, notably pharmaceutical compositions, containing polyethylene oxide and an active ingredient, and to methods for their preparation.

Certain medicaments need to be formulated in so-called delayed-release or sustained release form.

Polyethylene oxide referred to as PEO below is moreover known as a component of medicaments in tablet form designed to be administered by oral route. This compound is marketed by the Union Carbide Corporation under the commercial name Polyox®. The use of PEO for formulating medicaments has furthermore been the subject matter of many earlier patents.

EP-A-0 277 092, in the name of Ciba-Geigy relates to a composition comprising a casing in a material that is porous to water but not to the active ingredient, surrounding a central core consisting of a mixture of a substance that is weakly soluble in water, and a hydrophilic swelling material, said material consisting of a mixture of PEO and a vinyl pyrrolidone/vinyl acetate polymer. The composition in that patent is an example of current compositions in which a core which swells when exposed to water is surrounded by a water-porous material, release of the active ingredient being delayed or sustained as a result of the time necessary to expand the core, and for diffusion to take place through the casing following the penetration of water.

The abstract of the U.S. Pat No. 4,404,183 and U.S. Pat. No. 4,343,789 discloses two embodiments of a sustained release composition. In the first embodiment, the composition contains PEO, the active ingredient in an amorphous form, and a basic component. In the second embodiment, the active ingredient is nicardipine in an amorphous state, it being possible to omit the basic component.

Actually, the compositions according to the prior art are complex, require specific active ingredients or are provided in a specific form. Moreover, the results achieved are not always very good.

The present invention provides a simple composition which is suitable for use with a multiplicity of active ingredients, and has a remarkable delaying or sustaining effect.

Thus, the present invention provides a solid composition comprising, by weight based on the total weight of the composition:
 (a) from 1 to 70% of an active ingredient which is not in an amorphous form;
 (b) from 10 to 95% of polyethylene oxide;
 (c) the balance consisting of conventional additives, excluding basic components.

The expression "solid composition" means that the composition is in a tablet or mini-tablet form, these in their turn being able to be encapsulated using for example the conventional hard gelatin.

The expression "active ingredient" should be understood in its normal sense and, generally speaking, covers medicaments for treatment of the human or animal body as well as an association of one or several such medicaments. Active ingredients that are either hydrophilic or lipophilic are envisaged.

The expression "not in amorphous form" should be understood in its conventional meaning. Various sources give a definition of this term "amorphous" as meaning non-crystalline, lacking the lattice structure characterizing the crystalline state. The following references, which provide a definition of the term amorphous (or the opposite thereof) are, in a on-limiting manner : Hawley's, Condensed Chemical Dictionary, 12th Edition, p. 71; Handbook of Chemistry and Physics, 65th Edition, F-67; The Theory and Practice of Industrial Pharmacy, 1970, pp. 253–255; Remington's Pharmaceutical Sciences, 14th Edition, p. 182; General Chemistry 1992, pp.314–315; Encyclopedia of Pharmaceutical Technology, vol I, pp. 12–13.

The expression "excluding basic compounds" should be understood as excluding the presence of a compound or a group of compounds that confer a basic nature on the composition, in other words a pH greater than 7, when the composition is diluted in water at a rate of 10 g per liter of water. In particular, this term should be taken as excluding the presence of one or several basic component(s) such as described in column 1, lines 38 to 62 of U.S. Pat. No. 4,404,183 if no acid compound is counteracting the effect of said basic compound, or if the basic compound is present in a relatively large amount.

According to one preferred embodiment, the composition according to the invention, comprises:
 (a) from 5 to 45% of an active ingredient;
 (b) from 25 to 70% polyethylene oxide
 (c) the balance consisting of conventional additives, excluding basic components.

According to one preferred embodiment of the composition according to the invention, the active ingredient is a hydrophilic or lipophilic active ingredient, advantageously a hydrophilic ingredient.

According to another preferred embodiment of the composition according to the invention, the active ingredient is selected from the group comprising acyclovir, nifedipine, nicardipine, captopril, verapamil, diltiazem, oxybutynine, valacyclovir, glipizide, felodipine, isosorbide, carbidopa, levodopa, pentoxiphylline, and their pharmaceutically acceptable salts.

According to one alternative embodiment, in the composition according to the invention, the polyethylene oxide has a molecular weight which varies from 50,000 to 8,000,000, and preferably from 100,000 to 3,000,000. The required molecular weight for the PEO can be obtained by mixing PEO of differing molecular weights, that are available commercially.

According to a further embodiment, in the composition according to the invention, the balance consisting of conventional additives comprises microcrystalline cellulose, lactose, ascorbic acid, pigments, plastifying agents, lubricants and so on. Obviously, other conventional additives known to those skilled in the art can be employed.

According to one embodiment of the invention, in a composition, the balance consisting of conventional additives comprises magnesium stearate and/or glycerol behenate and/or sodium stearyl fumarate, which is employed as a lubricant ensuring better compression of the composition when provided in tablet form, for example.

According to one or alternative embodiment, the composition is additionally coated. Surface coating is employed for the purposes of improving appearance making the drug more readily acceptable to the patient, or for dimensionally stabilising the compressed tablet. The coating can be a conventional coating suitable for enteral use. It is obtained using any conventional technique employing conventional ingredients. A surface coating can for example be obtained using a quick-dissolving film. It should be noted that the coating according to this invention is fundamentally different from the coating used in EP-A-0,277,092 as one does not encounter, in the invention, the dichotomy (water-swellable core)/(water-porous coating), and moreover, the coating in the invention dissolves and/or disintegrates whereas the coating in EP-A-0,277,092 does not dissolve.

According to another embodiment, the coating is functional. This functional coating comprises a functional coating which comprises, based on the weight of the coating, from 30 to 80% of a gastroresistant polymer and from 10 to 40% of a hydrophilic silicon dioxide.

The gastroresistant polymer withstands the acidic medium of the stomach and the duodenum, but will dissolve in the intestines, as soon as the pH reaches a predetermined level (e.g. above 5.5 or above 7). This gastroresistant polymer can be selected from the group consisting in (uncured) poly(meth)acrylic acid, cellulose and alkylcellulose-phtalates. Molecular weight can vary within broad limits as will recognize the skilled man. The term "uncured" is used to differentiate over U.S. Pat. No. 5,580,578.

Preferably, it is of the type of Eudragit L30D55. One preferred polymer is an anionic copolymer on the basis of methacrylic acid and acrylic acid ethyl ester. The formula is as follows:

The ratio free carboxyl group to ester group is preferably about 1:1. The mean molecular weight is e.g. about 250,000.

Such a copolymer will easily dissolve at pH values above 5.5 with the forming of salts.

Hydrophilic silicon dioxide is a known hydrophilic anti-tacking agent, the definition of which is known to the skilled man and can be found in the literature.

The functional coating may further comprise polyethyleneglycol, present in an amount from 5 to 30% by weight, based on the total weight of the functional coating. Stearic acid, dibutyl sebacate, propylene glycol and/or triethyl citrate can used in lieu of or in addition to polyethyleneglycol.

The functional coating usually represents from 0.5 to 6% by weight of the core weight.

The present solid compositions are suitable for the administration of medicaments. Thus, the invention also relates to pharmaceutical compositions deriving therefrom as well as to compositions thereof for use as medicaments.

The present composition can be obtained by any conventional method known to those skilled in the art such as, for example direct compression after simply mixing the dry ingredients, moist or wet granulation involving the use of a granulation liquid, and dry granulation involving a densification phase for the dry mixture.

However, use is preferably made of a process comprising the steps of:
(i) mixing in the dry state and for a sufficient time, the active ingredient, polyethylene oxide and optionally, one or several additives;
(ii) optionally adding solvent when this is used, followed by mixing for a sufficient period of time;
(iii) granulation by passage through a suitable sieve;
(iv) drying the granules thus formed for a sufficient period of time;
(v) optionally adding one of more additives, with mixing in the dry state for a sufficient time and passage through a suitable sieve;
(vi) optionally adding one or several additives and mixing in the dry state for a sufficient period of time;
(vii) compressing the mixture obtained from the preceding steps to obtain the desired compressed tablet; and
(viii) optionally coating said compressed tablet.

The solvent employed, when use is made of a solvent, is preferably an alcohol. The solvent is eliminated by drying at one point or another in the process, and is substantially not encountered in the final composition.

The choice of mixing times, apparatus used, sieve mesh, and other operating conditions are within the province of the normal knowledge of those skilled in the art.

The invention will now be described in more detail, with reference to FIG. 1 which shows percentage in-vitro release of an active ingredient as a function of time for the solid compositions of examples 1 and 2.

Without wishing to be bound by any theory, the applicant believes that the PEO, in the formulation, forms a hydrogel from contact with water. This hydrogel dissolves more or less rapidly as a function of the molecular weight of the PEO employed. Choosing the molecular weight of the PEO, in combination with a suitable choice of the weight concentrations of the active ingredient, of PEO, and of additives enables release of the active ingredient to be controlled.

Moreover, the present composition exhibits particularly surprising results. In a hydrophilic matrix, when the concentration of the hydrophilic active ingredient increases, one would expect that the rate of release of the active ingredient would increase. The present composition exhibits the opposite effect, in the case, for example, of acyclovir as active ingredient. This is clearly shown in FIG. 1, which gives in-vitro dissolution of the compositions of examples 1 and 2. The composition of example 1 has a lower concentration of the active ingredient (200 mg medicament in a 905 mg tablet) and shows a faster in-vitro release of the drug as compared to the formulation of example 2 which has a higher concentration of the active ingredient (400 mg of medicament in a 905 mg tablet). This result is particularly surprising.

The examples below are provided as examples illustrating the invention and should not be considered as limiting its scope. In the examples, the amount of solvent employed is given in brackets, it being understood that the solvent is substantially absent in the final composition.

EXAMPLE 1

The following composition was prepared:

| | |
|---|---|
| Acyclovir | 200.0 mg |
| PEO (MW = 100 000) | 700.0 mg |
| Magnesium stearate | 5.0 mg |
| Industrial alcohol | (260.0 mg) |

The acyclovir and PEO are weighed and added to a mixer kneader. Mixing in the dry state is performed for 5 minutes. Alcohol is added to the mixture and followed by mixing by 5 minutes. Granulation is achieved by passing through a sieve of 1.6 mm mesh. The granules are dried and are passed through a 0.8 mm mesh sieve. After weighing, the magnesium stearate is added and mixing in the dry state is performed during 2 minutes. Tablets are obtained by compression using a Frogerais MR 15 machine.

EXAMPLE 2

The following composition is prepared:

| | |
|---|---|
| Acyclovir | 400.0 mg |
| PEO (MW = 100 000) | 500.0 mg |
| Magnesium stearate | 5.0 mg |
| Industrial alcohol | (260.0 mg) |

The acyclovir and PEO are weighed and added in a mixer kneader. Mixing in the dry state is performed for 5 minutes. Alcohol is added to the mixture and followed by mixing by 5 minutes. Granulation is achieved by passing through a sieve of 1.6 mm mesh. The granules are dried and are passed through a 0.8 mm mesh sieve. After weighing, the magnesium stearate is added and mixing in the dry state is performed during 2 minutes. Tablets are obtained by compression using a rotary Frogerais MR 15 type machine.

EXAMPLE 3

The following composition was prepared:

| | |
|---|---|
| Nifedipine | 60.0 mg |
| Microcristalline cellulose | 100.0 mg |
| PEO (MW = 3 000 000) | 336.0 mg |
| Colloidal silicon dioxide | 2.5 mg |
| Magnesium stearate | 2.5 mg |
| Industrial alcohol | (150.0 mg) |

The nifedipine, microcrystalline cellulose (available from the company FMC under the commercial name Avicel PH 101) and the PEO are weighed and added to a mixer kneader. They are mixed in the dry state for 5 minutes and the alcohol is added to the mixture with further mixing for 5 minutes. Granulation is performed by passage through a 1.8 mm mesh sieve. The granules are dried. The colloidal silicon dioxide (available from Degussa under the commercial name Aerosil 200) is weighed and added and mixing is carried out in the dry state for 5 minutes followed by passage through a 0.6 mm mesh sieve. The magnesium stearate is weighed and added with mixing in the dry state for 2 minutes. The tablets are obtained by compression in a rotary Frogerais MR 15 type machine.

EXAMPLE 4

| | |
|---|---|
| Core | |
| Nifedipine | 60.0 mg |
| Microcristalline cellulose | 100.0 mg |
| PEO (MW = 3 000 000) | 336.0 mg |
| Colloidal silicon dioxide | 2.5 mg |
| Magnesium stearate | 2.5 mg |
| Industrial alcohol | (150.0 mg) |
| Coating: | |
| Iron oxide | 2.0 mg |
| Titanium dioxide | 1.0 mg |
| Methylcellulose | 12.0 mg |
| Industrial alcohol | (150.0 mg) |

The nifedipine, microcrystalline cellulose (available from the company FMC under the commercial name Avicel PH 101) and the PEO are weighed and added to a mixer kneader. They are mixed in the dry state for 5 minutes and the alcohol is added to the mixture with further mixing for 5 minutes. Granulation is performed by passage through a 1.6 mm mesh sieve. The granules are dried. The colloidal silicon dioxide (available from Degussa under the commercial name Aerosil 200) is weighed and added and mixing is carried out in the dry state for 10 minutes followed by passage through a 0.8 mm mesh sieve. The magnesium stearate is weighed and added with mixing in the dry state for 2 minutes. The tablets are obtained by compression in a rotary Frogerais MR 15 type machine.

Following this, the methylcellulose (available from Colorcon under the commercial name Methocel) is dissolved in the alcohol. The iron oxide and titanium dioxide are added to the solution, followed by homogenization in an Ultra Turrax apparatus for 10 minutes. The tablets are coated by spraying this suspension in a perforated pan coating apparatus of the "Glatt coater" type.

EXAMPLE 5

The following composition is prepared:

| | |
|---|---|
| Core: | |
| Nicardipine.HCl | 60.0 mg |
| Microcrystalline cellulose | 77.0 mg |
| PEO (MW = 2 000 000) | 270.0 mg |
| Magnesium stearate | 3.0 mg |
| Industrial alcohol | (150.0 mg) |
| Coating: | |
| Iron oxide | 2.0 mg |
| Titanium dioxide | 1.0 mg |
| Methylcellulose | 12.0 mg |
| Industrial alcohol | (150.0 mg) |

The nicardipine.HCl, microcrystalline cellulose (Avicel PH 101) and PEO are weighed and added to a kneader. Mixing in the dry state is carried out for 5 minutes. The alcohol is added to the mixture with further kneading for 5 minutes. Granulation is carried out by passage through a 1.6 mm mesh sieve. The granules are dried and passed through a 0.8 mm mesh sieve. The magnesium stearate is weighed and added followed by dry mixing for 2 minutes. The tablets are obtained by compression in a rotary Frogerais MR 15 type machine.

Following this, the methylcellulose (Methocel) is dissolved in the alcohol. The iron oxide and titanium oxide are added to the solution followed by homogenization in an Ultra Turrax apparatus for 10 minutes. The tablets are coated by spraying this suspension in a Glatt coater type coating apparatus.

EXAMPLE 6

The following composition is prepared:

| | |
|---|---|
| Core: | |
| Captopril | 50.0 mg |
| Microcrystalline cellulose | 100.0 mg |
| PEO (MW = 2 500 000) | 300.0 mg |
| Ascorbic acid (powder) | 100.0 mg |
| Magnesium stearate | 3.0 mg |

-continued

| Coating: | |
|---|---|
| Titanium dioxide | 1.0 mg |
| Methylcellulose | 10.0 mg |
| Industrial alcohol | (150.0 mg) |

The captopril, microcristalline cellulose (Avicel 200), ascorbic acid and PEO are weighed and added to a mixer kneader. Dry mixing is carried out during 5 minutes, followed by a passage through 1.6 mm mesh sieve. The magnesium stearate is weighed and added with mixing in the dry state for 2 minutes. The tablets are obtained by compression in a rotary Frogerais MR 15 type machine.

Next, the methylcellulose (Methocel) is dissolved in the alcohol. The titanium dioxide is added to the solution followed by homogenization in an Ultra Turrax apparatus for 10 minutes. The tablets are spray coated with this suspension in a Glatt coater type coating apparatus.

EXAMPLE 7

The following composition is prepared:

| Verapamil.HCl | 240.0 mg |
|---|---|
| Lactose | 100.0 mg |
| PEO (MW = 1 000 000) | 200.0 mg |
| Magnesium stearate | 5.0 mg |
| Industrial alcohol | (200.0 mg) |

The Verapamil.HCl, lactose (available from the company HMS under reference 80 mesh) and the PEO are weighed and added to a mixer kneader followed by mixing in the dry state for 5 minutes. The alcohol is added to the mixture with further kneading for 5 minutes. Granulation is achieved by passage through a 1.6 mm mesh sieve. The granules are dried and passed through a 0.8 mm sieve. The magnesium stearate is weighed and added, with mixing in the dry state for 2 minutes. The tablets are obtained by compression in a rotary Frogerais MR 15 type machine.

EXAMPLE 8

The following composition is prepared:

| Diltiazem HCl | 180.0 mg |
|---|---|
| Lactose | 100.0 mg |
| PEO (MW = 1 500 000) | 160.0 mg |
| Magnesium stearate | 3.0 mg |
| Industrial alcohol | (150.0 mg) |

The diltiazem.HCl, lactose (HMS, 80 mesh) and PEO are weighed and added to a mixer kneader. Mixing is carried out in the dry state for 5 minutes. The alcohol is added to the mixture with mixing for 5 minutes. Granulation is achieved by passage through a 1.6 mm mesh sieve. The granules are dried and passed through a 0.8 mm sieve. The magnesium stearate is weighed and added, followed by mixing in the dry state for 2 minutes. The tablets are obtained by compression in a rotary Frogerais MR 15 type machine.

EXAMPLE 9

The following composition is prepared:

| Oxybutynine.HCl | 15.0 mg |
|---|---|
| Microcrystalline cellulose | 75.0 mg |
| PEO (MW = 1 000 000) | 120.0 mg |
| Colloidal silicon dioxide | 1.5 mg |
| Magnesium stearate | 1.5 mg |
| Industrial alcohol | (110.0 mg) |

The oxybutynine.HCl, microcrystalline cellulose (Avicel PH 101) and PEO are weighed and added to a mixer kneader. Mixing in the dry state is performed for 5 minutes. The alcohol is added to the mixture with further mixing for 5 minutes. Granulation is achieved by passage through a 1.6 mm mesh sieve. The granules are dried. The colloidal silicon dioxide (Aerosil 200) is weighed and added followed by mixing in the dry state for 10 minutes and passage through a 0.8 mm mesh sieve. The magnesium stearate is weighed and added, with mixing in the dry state for 2 minutes. The tablets are obtained by compression in a rotary Frogerais MR 15 type machine.

EXAMPLE 10

The following composition was prepared:

| Core: | |
|---|---|
| Nifedipine | 60.0 mg |
| Microcristalline cellulose | 100.0 mg |
| PEO (MW = 3 000 000) | 336.0 mg |
| Colloidal silicon dioxide | 2.5 mg |
| Magnesium stearate | 2.5 mg |
| Industrial alcohol | (150.0 mg) |
| Coating 1: | |
| Ammonio methacrylate copolymer type A | 160.0 mg |
| Hydroxy propyl methyl cellulose | 20.0 mg |
| Water | 30.0 g |
| Industrial alcohol | (150.0 mg) |
| Coating 2: | |
| Iron oxide | 2.0 mg |
| Titanium dioxide | 1.0 mg |
| Methylcellulose | 12.0 mg |
| Industrial alcohol | (150.0 mg) |

The method of preparing the core is identical to that described in Example 4.

Coating 1 is prepared as follows.

The hydroxy propyl methyl cellulose is weighed and dissolved in the water/alcohol mixture. The amminio methacrylate copolymer (USP XXIII, 12.5% solid available from Rohm Pharma, German under the commercial name Eudragit RL) is weighed and added followed by mixing. Coating is done in a Glatt coater type apparatus.

The method for preparing coating 2 and the application of the coating to the tablet obtained from the previous step are identical to those described in Example 4.

EXAMPLE 11

The following composition is prepared:

| | |
|---|---|
| Valacyclovir | 200.0 mg |
| PEO (MW = 300 000) | 700.0 mg |
| Magnesium stearate | 5.0 mg |
| Industrial alcohol | (260.0 mg |

The valacyclovir and PEO are weighed and added in a mixer kneader. Mixing in the dry state is performed for 5 minutes. Alcohol is added to the mixture, followed by mixing by 5 minutes. Granulation is achieved by passing through a sieve of 1.6 mm mesh. The granules are dried and are passed through a 0.8 mm mesh sieve. After weighing, magnesium stearate is added and mixing in the dry state is performed during 2 minutes. Tablets are obtained by compression using a Frogerais MR 15 type machine.

According to the general process disclosed in the previous examples, the following compositions are prepared, where the active ingredient is a crystalline powder.

EXAMPLE 12

The following composition was prepared:

| | |
|---|---|
| Core: | |
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 13

The following composition was prepared:

| | |
|---|---|
| Core: | |
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Ammonio methacrylate copolymer | 10.0 mg |
| Triethyl citrate | 3.0 mg |
| Polyethylene glycol | 1.0 mg |
| Hydroxypropylmethylcellulose | 7.0 mg |

EXAMPLE 14

The following composition was prepared:

| | |
|---|---|
| Core: | |
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Ammonio methacrylate copolymer | 10.0 mg |
| Lactose | 10.0 mg |
| Silicon dioxide | 4.0 mg |

EXAMPLE 15

The following composition was prepared:

| | |
|---|---|
| Core: | |
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| 30% polyacrylate dispersion | 15.0 mg |
| Silicon dioxide | 6.0 mg |
| Talc | 2.0 mg |
| Hydroxypropylmethylcellulose | 6.0 mg |

EXAMPLE 16

The following composition was prepared:

| | |
|---|---|
| Core: | |
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 17

The following composition was prepared:

| | |
|---|---|
| Core: | |
| Felodipine | 10.0 mg |
| PEO | 220.0 mg |
| Microcristalline cellulose | 55.0 mg |

-continued

| | |
|---|---|
| Hydroxy propyl methyl cellulose | 20.0 mg |
| Sodium stearyl fumarate | 1.7 mg |
| Coating: | |
| Ammonio methacrylate copolymer | 10.0 mg |
| Triethyl citrate | 3.0 mg |
| Polyethylene glycol | 1.0 mg |
| Hydroxypropylmethylcellulose | 7.0 mg |

EXAMPLE 18

The following composition was prepared:

| | |
|---|---|
| Core: | |
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| Ammonio methacrylate copolymer | 10.0 mg |
| Lactose | 10.0 mg |
| Silicon dioxide | 4.0 mg |

EXAMPLE 19

The following composition was prepared:

| | |
|---|---|
| Core: | |
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| 30% polyacrylate dispersion | 15.0 mg |
| Silicon dioxide | 6.0 mg |
| Talc | 2.0 mg |
| Hydroxypropylmethylcellulose | 6.0 mg |

EXAMPLE 20

The following composition was prepared:

| | |
|---|---|
| Core: | |
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 21

The following composition was prepared:

| | |
|---|---|
| Core: | |
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Ammonio methacrylate copolymer | 5.0 mg |
| Triethyl citrate | 1.5 mg |
| Polyethylene glycol | 0.5 mg |
| Hydroxypropylmethylcellulose | 3.5 mg |

EXAMPLE 22

The following composition was prepared:

| | |
|---|---|
| Core: | |
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Ammonio methacrylate copolymer | 5.0 mg |
| Lactose | 5.0 mg |
| Silicon dioxide | 2.0 mg |

EXAMPLE 23

The following composition was prepared:

| | |
|---|---|
| Core: | |
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| 30% polyacrylate dispersion | 7.5 mg |
| Silicon dioxide | 3.0 mg |
| Talc | 3.0 mg |
| Hydroxypropylmethylcellulose | 3.0 mg |

EXAMPLE 24

The following composition was prepared:

| | |
|---|---|
| Core: | |
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |

-continued

| | |
|---|---|
| PEO | 20.0 mg |
| Sodium stearyl fumarate | 1.7 mg |
| Coating: | |
| Methacrylic acid copolymer | 50.0 mg |
| Polyethylene glycol | 1.0 mg |
| Talc | 1.25 mg |
| Silicon dioxide | 2.25 mg |

EXAMPLE 25

The following composition was prepared:

| | |
|---|---|
| Core: | |
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| Ammonio methacrylate copolymer | 5.0 mg |
| Triethyl citrate | 1.5 mg |
| Polyethylene glycol | 0.5 mg |
| Hydroxypropylmethylcellulose | 3.5 mg |

EXAMPLE 26

The following composition was prepared:

| | |
|---|---|
| Core: | |
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| Ammonio methacrylate copolymer | 5.0 mg |
| Lactose | 5.0 mg |
| Silicon dioxide | 2.0 mg |

EXAMPLE 27

The following composition was prepared:

| | |
|---|---|
| Core: | |
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| 30% polyacrylate dispersion | 7.5 mg |
| Silicon dioxide | 3.0 mg |

-continued

| | |
|---|---|
| Talc | 1.0 mg |
| Hydroxypropylmethylcellulose | 3.0 mg |

EXAMPLE 28

The following composition was prepared:

| | |
|---|---|
| Core: | |
| Pentoxiphylline | 400.0 mg |
| PEO | 150.0 mg |
| Povidone | 30.0 mg |
| Glycerol behenate | 6.0 mg |
| Coating: | |
| Methacrylic acid copolymer | 20.0 mg |
| Polyethylene glycol | 4.0 mg |
| Talc | 5.0 mg |
| Silicon dioxide | 9.0 mg |

EXAMPLE 29

The following composition was prepared:

| | |
|---|---|
| Core: | |
| Pentoxiphylline | 400.0 mg |
| PEO | 150.0 mg |
| Povidone | 30.0 mg |
| Glycerol behenate | 6.0 mg |
| Coating: | |
| Ammonio methacrylate copolymer | 20.0 mg |
| Triethyl citrate | 6.0 mg |
| Polyethylene glycol | 2.0 mg |
| Hydroxypropylmethylcellulose | 14.0 mg |

EXAMPLE 30

The following composition was prepared:

| | |
|---|---|
| Core: | |
| Pentoxiphylline | 400.0 mg |
| PEO | 150.0 mg |
| Povidone | 30.0 mg |
| Glycerol behenate | 6.0 mg |
| Coating: | |
| Ammonio methacrylate copolymer | 20.0 mg |
| Lactose | 20.0 mg |
| Silicon dioxide | 8.0 mg |

EXAMPLE 31

The following composition was prepared:

| | |
|---|---|
| Core: | |
| Pentoxiphylline | 400.0 mg |
| PEO | 150.0 mg |

-continued

| | |
|---|---|
| Povidone | 30.0 mg |
| Glycerol behenate | 6.0 mg |
| Coating: | |
| 30% polyacrylate dispersion | 30.0 mg |
| Silicon dioxide | 12.0 mg |
| Talc | 4.0 mg |
| Hydroxypropylmethylcellulose | 12.0 mg |

EXAMPLE 32

The following composition was prepared:

| | |
|---|---|
| Core: | |
| Nicardipine | 30.0 mg |
| PEO | 150.0 mg |
| Microcristalline cellulose | 30.0 mg |
| Povidone | 30.0 mg |
| Magnesium stearate | 2.0 mg |
| Coating: | |
| Methacrylic acid copolymer | 6.0 mg |
| Polyethylene glycol | 1.2 mg |
| Talc | 1.5 mg |
| Silicon dioxide | 2.7 mg |

EXAMPLE 33

The following composition was prepared:

| | |
|---|---|
| Core: | |
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| Ammonio methacrylate copolymer | 6.0 mg |
| Triethyl citrate | 1.8 mg |
| Polyethylene glycol | 0.6 mg |
| Hydroxypropylmethylcellulose | 4.2 mg |

EXAMPLE 34

The following composition was prepared:

| | |
|---|---|
| Core: | |
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| Ammonio methacrylate copolymer | 6.0 mg |
| Lactose | 6.0 mg |
| Silicon dioxide | 2.4 mg |

EXAMPLE 35

The following composition was prepared:

| | |
|---|---|
| Core: | |
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| 30% polyacrylate dispersion | 9.0 mg |
| Silicon dioxide | 3.6 mg |
| Talc | 1.2 mg |
| Hydroxypropylmethylcellulose | 3.6 mg |

EXAMPLE 36

The following composition was prepared:

| | |
|---|---|
| Core: | |
| Nifedipine | 90.0 mg |
| PEO (900,000) | 162.0 mg |
| PEO (200,000) | 18.0 mg |
| Microcristalline cellulose | 39.5 mg |
| Silicon dioxide | 1.8 mg |
| Povidone | 6.5 mg |
| Magnesium stearate | 1.8 mg |
| Vitamin E | 0.4 mg |

The core is manufactured as follows:

Nifedipine, PEOs and microcristalline cellulose are mixed in a high shear mixer (T. K. Fielder). Povidone and Vit. E are dissolved in denatured alcohol and this solution is added to the mixture of Nifedipine, PEOs and microcristalline cellulose under high shear mixing. The wet mass thus obtained is passed through a sieve (co-mill) and is dried as granules. Silicon dioxide and magnesium stearate are added to the dry granules and are blended in a dry mixer (cone blender) and is compressed to tablets in a rotary tablet press (Fette).

The dissolution profile has been determined (medium is 1000 ml 2% sodium lauryl sulfate in a phosphate buffer pH=6.8, basket 100 rpm). The results are the following:

| Time (hr) | % dissolved |
|---|---|
| 4 | 31 |
| 8 | 71 |
| 12 | 98 |

EXAMPLE 37

The following composition was prepared:

| | |
|---|---|
| Core: | |
| Nifedipine | 90.0 mg |
| PEO (MW 3,000,000) | 336.0 mg |
| Silicon dioxide | 2.5 mg |

-continued

| Core: | |
|---|---|
| Microcristalline cellulose | 100.0 mg |
| Magnesium stearate | 2.5 mg |

The core is manufactured as in example 4.

A coating is applied on said core. The coating has the following composition:

| Coating: | |
|---|---|
| Eudragit L30D | 15.0 mg |
| Fumed silica | 3.0 mg |
| PEG 8000 | 4.5 mg |

The coating mixture is prepared by suspending silica in water and homogenizing with a Ultra Turrex, then dissolving PEG in the mixture and adding the Eudragit to this under gentle mixing (propeller mixer). The tablets are coated in a perforated pan coater (O'Hara) by spraying the coating mixture.

The dissolution profile has been determined (medium is 1000 ml 1.25% Tween in water, basket 150 rpm). The results are the following:

| Time (hr) | % dissolved |
|---|---|
| 4 | 13 |
| 12 | 70 |
| 24 | 99 |

EXAMPLE 38

The following composition was prepared, in a manner similar to the one disclosed in example 37:

| Core: | |
|---|---|
| Glipizide | 10.0 mg |
| PEO (2,000,000) | 200.0 mg |
| Povidone | 10.0 mg |
| Silicon dioxide | 3.0 mg |
| Microcristalline cellulose | 76.5 mg |
| Sodium stearyl fumarate | 6.0 mg |
| Vitamin E | 0.6 mg |
| Coating: | |
| Eudragit L30D | 7.04 mg |
| Fumed silica | 2.8 mg |
| PEG 1450 | 1.44 mg |
| Triethyl citrate | 0.72 mg |

The dissolution profile has been determined (medium is 1000 ml phosphate buffer pH=6.8, paddle 150 rpm, special sinking basket). The results are the following:

| Time (hr) | % dissolved |
|---|---|
| 4 | 20 |
| 8 | 51 |
| 12 | 95 |

EXAMPLE 39

The following composition was prepared, in a manner similar to the one disclosed in example 36

| Core: | |
|---|---|
| Felodipine | 10.0 mg |
| PEO (900,000) | 153.0 mg |
| PEO (200,000) | 27.0 mg |
| Microcristalline cellulose | 24.0 mg |
| Silicon dioxide | 1.1 mg |
| Povidone | 6.8 mg |
| Sodium stearyl fumarate | 2.2 mg |
| Vitamin E | 0.9 mg |

The coating is a non-functional classical Opadry® coating (see example 4 for manufacture).

The dissolution profile has been determined (medium is 750 ml 1% sodium lauryl sulfate in a phosphate buffer pH=6.8, basket 100 rpm). The results are the following:

| Time (hr) | % dissolved |
|---|---|
| 4 | 37 |
| 8 | 70 |
| 12 | 95 |

What is claimed is:

1. A solid composition comprising, by weight based on the total weight of the composition:
   (a) from 1 to 15% of glipizide which is not in an amorphous form;
   (b) from 60 to 80% of polyethylene oxide;
   (c) the balance consisting of conventional additives, excluding basic components; and
   (d) a functional coating comprising, based on the weight of the coating, from 30 to 80% of a gastroresistant polymer and from 10 to 40% of a hydrophilic silicon dioxide;
exhibiting a dissolution profile such that after 4 hours, from 10 to 30% of the glipizide is released, after 8 hours, from 40 to 60% of the glipizide is released, after 12 hours, from 80 to 100% of the glipizide is released.

2. The composition according to claim 1, in which the polyethylene oxide has a molecular weight which varies from 50,000 to 8,000,000.

3. The composition according to claim 2, in which the polyethylene oxide has a molecular weight which varies from 100,000 to 3,000,000.

4. The composition according to claim 1, in which, in the functional coating, the gastroresistant polymer is comprised of uncured poly(meth)acrylic acid.

5. The composition according to claim 1, in which the functional coating further comprises polyethyleneglycol, present in an amount from 5 to 30% by weight, based on the total weight of the functional coating.

6. The composition according to claim 1, in which the balance consisting of conventional additives comprises microcrystalline cellulose, lactose, pigments, plastifying agents, lubricants, and others.

7. The composition according to claim 1, in which the balance consisting of conventional additives comprises magnesium stearate and/or glycerol behenate and/or sodium stearyl fumarate.

8. A solid composition comprising, by weight based on the total weight of the composition:
   (a) from 1 to 15% of glipizide which is not in an amorphous form;
   (b) from 60 to 80% of polyethylene oxide;
   (c) the balance consisting of conventional additives, excluding basic components; and
   (d) a functional coating comprising, based on the weight of the coating, from 30 to 80% of a gastroresistant polymer comprised of uncured poly(meth)acrylic acid; from 10 to 40% of a hydrophilic silicon dioxide and from 5 to 30% of polyethyleneglycol;

exhibiting a dissolution profile such that after 4 hours, from 10 to 30% of the glipizide is released, after 8 hours, from 40 to 60% of the glipizide is released, after 12 hours, from 80 to 100% of the glipizide is released.

* * * * *

UNITED STATES PATENT AND TRADEMARK OFFICE
CERTIFICATE OF CORRECTION

Figure 1:
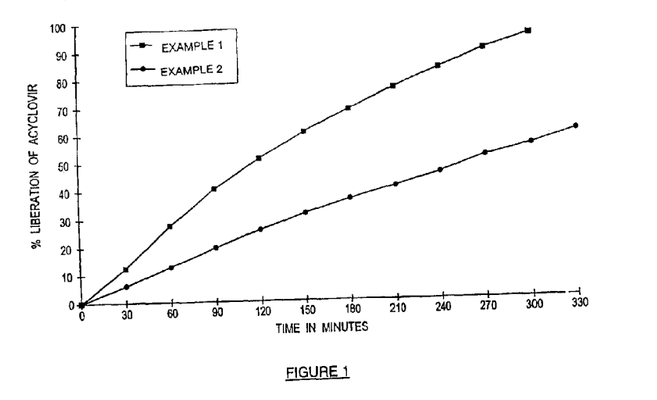

PATENT NO.   : 6,348,469 B1
DATED         : February 19, 2002
INVENTOR(S) : Pawan Seth It is certified that error appears in the above-identified patent and that said Letters Patent is hereby corrected as shown below:

Drawings,
Please replace old "Figure 1" with the following new -- Figure 1 --.

FIGURE 1

Signed and Sealed this

Twentieth Day of January, 2004

JON W. DUDAS
*Acting Director of the United States Patent and Trademark Office*